(12) United States Patent
Aubrun et al.

(10) Patent No.: US 8,636,990 B2
(45) Date of Patent: *Jan. 28, 2014

(54) USE OF EXPANDED AMORPHOUS MINERAL PARTICLES FOR INCREASING THE TENACITY OF A FRAGRANCE, SCENTING COMPOSITION AND METHOD FOR TREATING BODY ODOURS

(75) Inventors: Odile Aubrun, Antony (FR); Matthieu Cassier, Paris (FR)

(73) Assignee: L'Oreal, Paris (FR)

( * ) Notice: Subject to any disclaimer, the term of this patent is extended or adjusted under 35 U.S.C. 154(b) by 648 days.

This patent is subject to a terminal disclaimer.

(21) Appl. No.: 12/620,236

(22) Filed: Nov. 17, 2009

(65) Prior Publication Data

US 2010/0196484 A1    Aug. 5, 2010

Related U.S. Application Data

(60) Provisional application No. 61/116,802, filed on Nov. 21, 2008.

(30) Foreign Application Priority Data

Nov. 17, 2008   (FR) ...................... 08 57790

(51) Int. Cl.
*A61Q 13/00* (2006.01)
*A61K 8/28* (2006.01)
*A61Q 15/00* (2006.01)
*A61K 8/26* (2006.01)

(52) U.S. Cl.
USPC ............... 424/65; 424/401; 424/489; 424/66; 424/67; 424/68; 512/1

(58) Field of Classification Search
USPC .................. 424/489, 65, 401; 512/1
See application file for complete search history.

(56) References Cited

U.S. PATENT DOCUMENTS

| | | | |
|---|---|---|---|
| 2,778,774 A | 1/1957 | Buslik et al. | |
| 3,201,099 A * | 8/1965 | Carpenter | 432/58 |
| 4,786,369 A * | 11/1988 | Kanfer et al. | 510/399 |
| 4,803,195 A * | 2/1989 | Holzner | 512/4 |
| 5,421,291 A | 6/1995 | Lawson et al. | |
| 6,776,803 B2 * | 8/2004 | Oshika et al. | 8/405 |
| 7,202,201 B1 * | 4/2007 | Williams | 510/191 |
| 2003/0074743 A1 * | 4/2003 | Noguchi et al. | 8/401 |
| 2004/0111810 A1 * | 6/2004 | Kaizuka | 8/405 |
| 2007/0251024 A1 * | 11/2007 | Greaves et al. | 8/405 |

FOREIGN PATENT DOCUMENTS

| | | |
|---|---|---|
| DE | 12 89 600 B | 2/1969 |
| DE | 3824940 A1 | 1/1990 |
| DE | 103 56 692 A1 | 3/2005 |
| EP | 0770373 A1 | 5/1997 |
| FR | 2722101 A1 | 1/1996 |
| GB | 1057316 A | 2/1967 |
| JP | 55148560 A | 11/1980 |
| JP | 61087618 A | 5/1986 |
| JP | 5310546 A | 11/1993 |
| RU | 1790601 A3 | 1/1993 |

OTHER PUBLICATIONS

Pennsylvania Perlite Corporation, Accessed Jan. 22, 2013, pp. 1-2, http://www.pennperlite.com/uses.html.*
XP002538080 "Mixing granular perfumes to give desired aroma—by allowing different colour, porous particulates to hold perfumes corresp. To colours and mixing granular perfumes" (Abstract of JP 61 087618).
XP002538081 "Deodorant with high active at normal temp.—comprises hydrated glyoxal and expanded vermiculite in powder, paste or slurry form etc." (Abstract of JP 55 148560).
XP002538082 "Fumigant perfume compsn. Emitting little smoke on buring—comprises base of e.g. coal ash, active alumina or silica gel supporting the perfume" (Abstract of JP 05 310546).

* cited by examiner

*Primary Examiner* — Rachael E Bredefeld
(74) *Attorney, Agent, or Firm* — Novak Duce Connolly Bove + Quigg LLP

(57) ABSTRACT

The subject-matter of the invention is a cosmetic method for scenting a human keratinous substance which consists in applying, to the said substance, a scenting composition comprising, in a cosmetically acceptable medium, at least 0.3% by weight of at least one scenting substance and at least particles of an expanded amorphous mineral material and in particular of an expanded amorphous mineral material resulting from at least one volcanic rock and more particularly expanded perlite particles.

Another subject-matter of the present invention is a cosmetic method for treating human body odors, in particular axillary odors, which consists in applying, to the surface of the skin, an effective amount of the said composition.

The invention relates to specific scenting compositions comprising, in a cosmetically acceptable medium:
a) at least 0.3% by weight, with respect to the total weight of the composition, of a scenting substance;
b) at least the said particles.

14 Claims, No Drawings

USE OF EXPANDED AMORPHOUS MINERAL PARTICLES FOR INCREASING THE TENACITY OF A FRAGRANCE, SCENTING COMPOSITION AND METHOD FOR TREATING BODY ODOURS

CROSS REFERENCE TO RELATED APPLICATIONS

This application claims priority to FR 0857790 filed Nov. 17, 2008 and claims the benefit of U.S. Provisional Appl. No. 61/116,802 filed Nov. 21, 2008 the entire contents of all are hereby incorporated by reference.

A subject-matter of the invention is a cosmetic method for scenting a human keratinous substance which consists in applying, to the said substance, a scenting composition comprising, in a cosmetically acceptable medium, at least 0.3% by weight of at least one scenting substance and at least particles of an expanded amorphous mineral material and in particular of an expanded amorphous mineral material resulting from at least one volcanic rock and more particularly expanded perlite particles.

Another subject-matter of the present invention is a cosmetic method for treating human body odours, in particular axillary odours, which consists in applying, to the surface of the skin, an effective amount of the said composition.

The invention relates to specific scenting compositions comprising, in a cosmetically acceptable medium:
a) at least 0.3% by weight, with respect to the total weight of the composition, of a scenting substance;
b) at least the said particles.

It is known that a fragrance is the combination of various odorous substances which evaporate at different periods. Each fragrance exhibits what is known as a "top note", which is the odour which first diffuses when the fragrance is applied or when the receptacle comprising it is opened, a "heart or body note", which corresponds to the complete fragrance (emission for several hours after the "top note"), and a "base note", which is the most persistent odour (emission for several hours after the "heart note"). The persistence of the base note corresponds to the tenacity of the fragrance.

From time immemorial, human beings have attempted to wear fragrance and to scent the objects which surround them or the places in which they are found, both to mask strong and/or unpleasant odours and to give a pleasant odour.

The important criteria of quality which are sought for in scenting products include, on the one hand, the tenacity of the fragrance, namely the persistence of the base note on the skin, and, on the other hand, the transparency of the formulation and its fluid nature, for reasons of attractiveness and comfort of application.

It is also known to put fragrances into deodorant compositions intended to treat human body odours, in particular axillary odours.

The need remains to find novel types of agents which make it possible to effectively increase the tenacity of the fragrance in a broad range of scenting products, such as eaux de toilette, eaux de parfum, deodorant products and antiperspirant products, without the abovementioned disadvantages and without harming the comfort of the consumer, such as the feel.

It is known that unexpanded and unmilled perlite with a mean size ranging from 0.1 to 15 mm has been provided in Patent DE3824940 as matrix incorporating essential oils, aromas or disinfectants. However, this type of material is difficult to formulate in sprays and aerosols owing to the fact that it has a tendency to block the spraying devices. This type of material is not very satisfactory from the sensory cosmetic viewpoint with regard to the consumer due to its highly abrasive nature.

The Applicant Company has discovered, surprisingly, that this objective can be achieved by using particles of an expanded amorphous mineral material comprising at least two elements among silicon, aluminium and magnesium and in particular of an expanded amorphous mineral material resulting from at least one volcanic rock and more particularly expanded perlite particles in a scenting composition comprising, in a cosmetically acceptable medium, at least 0.3% by weight, with respect to the total weight of the composition, of a scenting substance.

The Applicant Company has also discovered, surprisingly, that the particles composed of a specific expanded amorphous mineral material constitute a good agent for treating perspiration and can be easily formulated in numerous products intended to reduce perspiration.

These discoveries form the basis of the invention.

A subject-matter of the invention is, on the one hand, a cosmetic method for scenting a human keratinous substance which consists in applying, to the said substance, a scenting composition comprising, in a cosmetically acceptable medium, at least 0.3% by weight of at least one scenting substance and at least particles of an expanded amorphous mineral material and in particular of an expanded amorphous mineral material resulting from at least one volcanic rock and more particularly expanded perlite particles.

Another subject-matter of the present invention is a cosmetic method for treating human body odours, in particular axillary odours, which consists in applying, to the surface of the skin, an effective amount of the said composition.

"Human keratinous substance" is understood to mean the skin, hair, scalp, eyelashes, eyebrows, nails or lips.

"Scenting substance" is understood to mean any fragrance or aroma capable of giving off a pleasant odour.

"Cosmetically acceptable medium" is understood to mean, in the composition of the invention, a nontoxic medium capable of being applied to the skin (including the inside of the eyelids), lips, nails, hair, eyelashes and eyebrows of human beings.

"Mineral material" is understood to mean, within the meaning of the invention, any material composed of inorganic substances.

"Amorphous" is understood to mean any material comprising less than 10% by weight of crystalline phase and preferably less than 5% by weight of crystalline phase, indeed even a totally noncrystalline material not having an ordered atomic structure.

"Expanded material" is understood to mean any material having a loose bulk density at 25° C. ranging from 10 to 400 kg/m$^3$ (Standard DIN 53468). This density can in particular be the result of a treatment by a thermal process, in particular at a temperature ranging from 700 to 1500° C. and preferably from 800 to 1100° C.

Use may be made, as scenting substance, in the composition of the invention, of fragrances and aromas of natural or synthetic origin and their mixtures. Mention may be made, as fragrances and aromas of natural origin, for example, of extracts of flowers (lily, lavender, rose, jasmine, ylang-ylang), of stalks and leaves (patchouli, geranium, bitter orange), of fruits (coriander, anise, cumin, juniper berry), of fruit peels (bergamot, lemon, orange), of roots (angelica, celery, cardamom, iris, sweet flag), of wood (pinewood, sandalwood, guaiac, pink cedar), of grasses and graminae (tarragon, lemon grass, sage, thyme), of needles and branches (spruce, fir, pine, dwarf pine) or of resins and balms (galbanum, elemi, benzoin, myrrh, oliban, opopanax).

Mention may be made, as scenting substance of synthetic origin, for example, of compounds of the ester, ether, aldehyde, ketone, aromatic alcohol and hydrocarbon type.

Mention may in particular be made, as esters, of benzyl acetate, benzyl benzoate, phenoxyethyl isobutyrate, p-(tert-butyl)cyclohexyl acetate, citronellyl acetate, citronellyl formate, geranyl acetate, linalyl acetate, dimethylbenzylcarbinyl acetate, phenylethyl acetate, linalyl benzoate, benzyl formate, ethylmethylphenyl glycinate, alkylcyclohexyl propionate, styrallyl propionate and benzyl salicylate.

Mention may be made, as ethers, of benzyl ethyl ether.

Mention may be made, as aldehydes, for example, of linear alkanals comprising from 8 to 18 carbon atoms, citral, citronellal, citronellyl oxyacetaldehyde, cyclamen aldehyde, hydroxycitronellal, lilial and bourgeonal.

Mention may be made, as ketones, for example, of ionones, such as α-isomethyl ionone, and methyl cedryl ketone.

Mention may be made, among aromatic alcohols and in particular terpene alcohols, of anethole, citronellol, eugenol, isoeugenol, geraniol, linalool, phenylethyl alcohol and terpineol.

Mention may in particular be made, as hydrocarbons, of terpenes. These compounds often exist in the form of mixtures of two or more of these odorous substances.

Furthermore, use may also be made of essential oils, components of aromas, such as, for example, essential oils of sage, camomile, clove, melissa balm, mint, cinnamon tree leaves, lime blossom, juniper, vetiver, olibanum, galbanum, labdanum and lavandin.

Use is preferably made, as scenting substance, alone or as a mixture, of essential oil of bergamot, dihydromyrcenol, lilial, lyral, citronellol, phenylethyl alcohol, α-hexylcinnamaidehyde, geraniol, benzylacetone, cyclamen aldehyde, linalool, ambroxan, indole, hedione, sandelice, essential oils of lemon, of mandarin and of orange, allylamine glycolate, cyclovertal, essential oil of lavandin, essential oil of sage, beta-damascone, essential oil of geranium, cyclohexyl salicylate, phenylacetic acid, geranyl acetate, benzyl acetate or rose oxide.

According to a preferred embodiment of the invention, use is made of a mixture of different scenting substances which together produce an agreeable note for the user. Mention may be made, among known olfactory notes, for example, of hesperidic fragrances, aromatic ones, floral fragrances, musky ones, fruity fragrances, spicy ones, oriental fragrances, sea fragrances, aquatic notes, chypre fragrances, woody fragrances, fougere ones and their mixtures.

Preferably, the amount of scenting substance(s) varies from 0.5 to 30% by weight, better still from 1 to 25% by weight, with respect to the total weight of the composition.

Expanded Amorphous Mineral Material

The expanded amorphous mineral material in accordance with the invention comprises at least two elements chosen from silicon, aluminium and magnesium.

The expanded mineral material resulting from at least one volcanic rock in accordance with the present invention generally comprises, in its composition, at least two elements chosen from silicon, aluminium and magnesium. It is capable of being obtained by thermal expansion of a volcanic rock comprising from 1 to 10% by weight of water and preferably from 1 to 5% by weight of water and less than 10% by weight of crystalline rock, with respect to the total weight of the composition of the rock, preferably followed by a milling.

The temperature of the expansion process can vary from 700 to 1500° C. and preferably from 600 to 1100° C. Use may in particular be made of the expansion process described in U.S. Pat. No. 5,002,698.

Volcanic or "effusive" rocks are generally produced by the rapid cooling of the liquid magma on contact with the air or water (quenching phenomenon, giving a hyaline rock). The volcanic rocks which can be used according to the present invention are chosen from those defined according to Streckeisen classification (1974).

Mention may in particular be made, among these volcanic rocks, of trachytes, latites, andesites, basalts, rhyolites or dacites. Use will more particularly be made of rhyolites and dacites and more particularly still of rhyolites.

According to a specific form of the invention, the particles of expanded amorphous mineral material exhibit a coefficient of expansion of 2 to 70.

Preferably, the particles of expanded amorphous mineral material exhibit a loose bulk density at 25° C. ranging from 10 to 300 kg/m$^3$ (Standard DIN 53468).

According to a specific form of the invention, the particles of expanded amorphous mineral material exhibit a spontaneous pH, measured at 25° C. in a 10% by weight dispersion in water, ranging from 6 to 8.

According to another specific form of the invention, the particles of expanded amorphous mineral material exhibit a silica content of greater than or equal to 65% by weight, with respect to the total weight of the composition of the material.

According to another specific form of the invention, the particles of expanded amorphous mineral material exhibit a particle size defined by a median diameter $D_{50}$ ranging from 0.5 to 50 μm and preferably from 0.5 to 40 μm.

Preferably, the particles of expanded amorphous mineral material exhibit a platelet form.

According to a specific form of the invention, the choice will be made, as particles of an expanded amorphous material, of expanded perlite particles.

The perlites which can be used according to the invention are generally aluminosilicates of volcanic origin and have, as composition:

70.0-75.0% by weight of silica $SiO_2$
12.0-15.0% by weight of aluminium oxide $Al_2O_3$
3.0-5.0% of sodium oxide $Na_2O$
3.0-5.0% of potassium oxide $K_2O$
0.5-2% of iron oxide $Fe_2O_3$
0.2-0.7% of magnesium oxide MgO
0.5-1.5% of calcium oxide CaO
0.05-0.15% of titanium oxide $TiO_2$ The perlite is milled, dried and then graded in a first stage. The product obtained, referred to as perlite ore, is grey in colour and has a size of the order of 100 μm.

The perlite ore is subsequently expanded (1000° C./2 seconds) to give more or less white particles. When the temperature reaches 850-900° C., the water trapped in the structure of the material vaporizes and results in the expansion of the material with respect to its original volume. The expanded perlite particles in accordance with the invention can be obtained by the expansion process described in U.S. Pat. No. 5,002,698.

Preferably, the perlite particles used will be milled; they are in this case referred to as expanded milled perlite (EMP). They preferably have a particle size defined by a median diameter $D_{50}$ ranging from 0.5 to 50 μm and preferably from 0.5 to 40 μm.

Preferably, the perlite particles used exhibit a loose bulk density at 25° C. ranging from 10 to 400 kg/m$^3$ (Standard DIN 53468) and preferably from 10 to 300 kg/m$^3$.

Preferably, the expanded perlite particles according to the invention have a water absorption capacity, measured at the wet point, ranging from 200 to 1500%, preferably from 250 to 800%.

The wet point corresponds to the amount of water which it is necessary to add to 1 g of particles in order to obtain a homogenous paste. This method derives directly from that of the uptake of oil applied to solvents. The measurements are taken in the same way via the wet point and the flow point, respectively having as following definition:

Wet Point: weight, expressed in grams per 100 g of product, corresponding to the production of a homogeneous paste during the addition of a solvent to a powder.

Flow Point: weight, expressed in grams per 100 g of product, from which the amount of solvent is greater than the ability of the powder to retain it. This is reflected by the production of a more or less homogenous mixture which flows over the glass plate.

The wet point and the flow point are measured according to the following protocol:

Protocol for Measuring the Water Absorption
1) Equipment Used
Glass plate (25×25 mm)
Spatula (wooden shaft and metal part (15×2.7 mm))
Brush with silk hairs
Balance
2) Procedure The glass plate is placed on the balance and 1 g of perlite particles are weighed out. The beaker containing the solvent and the liquid sampling pipette is placed on the balance. The solvent is gradually added to the powder while regularly kneading the combination (every 3 to 4 drops) using the spatula. The weight of solvent necessary to obtain the wet point is recorded. Solvent is again added and the weight which makes it possible to arrive at the flow point is recorded. The mean over 3 tests will be produced.

Use will in particular be made of the expanded perlite particles sold under the trade names Optimal 1430 OR or Optimal 2550 by World Minerals.

The amount of expanded amorphous mineral particles used according to the invention can advantageously represent from 1 to 40% by weight and in particular from 1 to 25% by weight of the total weight of the composition.

Volatile Compounds

The compositions according to the invention can additionally comprise at least one volatile compound.

The volatile compounds of the invention are volatile cosmetic compounds which are liquid at ambient temperature and which have a nonzero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

Mention may be made, among volatile compounds which can be used in accordance with the invention, of volatile alcohols preferably chosen from lower $C_1$-$C_5$ monoalcohols can be chosen from methanol, ethanol, propanol, isopropanol, n-butanol, isobutanol or t-butanol and more particularly ethanol.

Mention may also be made, as example of volatile hydrocarbon compounds which can be used in the invention, of volatile hydrocarbon oils chosen from hydrocarbon oils having from 8 to 16 carbon atoms, in particular $C_8$-$C_{16}$ isoalkanes of petroleum origin (also known as isoparaffins), such as isododecane (also known as 2,2,4,4,6-pentamethylheptane), isodecane or isohexadecane, for example the oils sold under the Isopar and Permethyl trade names, branched $C_8$-$C_{16}$ esters, isohexyl neopentanoate and their mixtures. Other volatile hydrocarbon oils, such as petroleum distillates, in particular those sold under the name Shell Solt by Shell, can also be used; volatile linear alkanes, such as those described in the patent application of Cognis in patent applications DE10 2008 012 457 and WO2008/155059.

Mention may be made, as an example of volatile silicone compounds which can be used in the invention, of volatile silicones, such as, for example, volatile linear or cyclic silicone oils, in particular those having a viscosity ≤8 centistokes ($8×10^{-6}$ $m^2/s$) and having in particular from 2 to 7 silicon atoms, these silicones optionally comprising alkyl or alkoxy groups having from 1 to 10 carbon atoms. Mention may in particular be made, as volatile silicone oil which can be used in the invention, of octamethyl-cyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane or dodecamethylpentasiloxane.

Mention may also be made of volatile linear alkyltrisiloxane oils of general formula (I):

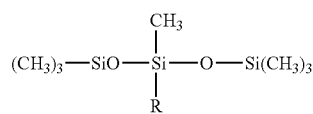

where R represents an alkyl group comprising from 2 to 4 carbon atoms, one or more hydrogen atoms of which can be replaced by a fluorine or chlorine atom.

Mention may be made, among the oils of general formula (I), of: 3-butyl-1,1,1,3,5,5,5-heptamethyltrisiloxane, 3-propyl-1,1,1,3,5,5,5-heptamethyltrisiloxane, and 3-ethyl-1,1,1,3,5,5,5-heptamethyltrisiloxane, corresponding to the oils of formula (I) for which R is respectively a butyl group, a propyl group or an ethyl group.

Deodorant Active Principles/Antiperspirant Salts or Complexes

According to a particularly preferred form of the invention, the scenting compositions additionally comprise at least one deodorant active principle and/or at least one antiperspirant salt or complex.

a/ Deodorants

Within the meaning of the present invention, "deodorant active principle" is understood to mean any substance capable of masking, absorbing, improving or reducing the unpleasant odour resulting from the decomposition of human sweat by bacteria.

The deodorant active principles can be bacteriostatic agents or bactericidal agents, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (® Triclocarban) or 3,7,11-trimethyldodeca-2,5,10-trienol (®Farnesol); quaternary ammonium salts, such as cetyltrimethylammonium salts or cetylpyridinium salts, DPTA (1,3-diaminopropanetetraacetic acid) or 1,2-decanediol (Simclariol from Symrise).

Mention may also be made, among the deodorant active principles in accordance with the invention, of:
zinc salts, such as zinc salicylate, zinc gluconate, zinc pidolate, zinc sulphate, zinc chloride, zinc lactate or zinc phenolsulphonate;
chlorhexidine and its salts;
sodium bicarbonate;

salicylic acid and its derivatives, such as 5-(n-octanoyl) salicylic acid;

glycerol derivatives, such as, for example, caprylic/capric glycerides (Capmul MCM from Abitec), glycerol caprylate or caprate (Dermosoft GMCY and Dermosoft GMC respectively from Straetmans) or polyglyceryl-2 caprate (Dermosoft DGMC from Straetmans);

biguanide derivatives, such as polyhexamethylene-biguanide salts;

silver, zeolites or silver-free zeolites.

In the event of incompatibility or in order to stabilize them, some of the active principles mentioned above can be incorporated in spherules, in particular vesicles, which may be ionic or nonionic, and/or nanoparticles (nanocapsules and/or nanospheres).

The deodorant active principles can preferably be present in the compositions according to the invention in concentrations by weight ranging from 0.01 to 5% by weight, with respect to the total weight of the composition.

In order to improve the antiperspirant effectiveness of the composition, use may additionally be made of one or more water-soluble anionic polymers comprising a Bronsted acid, in particular those deriving from maleic acid and/or maleic anhydride which are described in Patent Application WO 02/49590.

b/ Antiperspirant Salts or Complexes

"Antiperspirant salt or complex" is understood to mean any salt or complex which, by itself alone, has the effect of reducing or limiting the flow of sweat and/or absorbing human sweat.

The antiperspirant salts or complexes in accordance with the invention are generally chosen from aluminium and/or zirconium salts or complexes. They are preferably chosen from aluminium hydrohalides; aluminium zirconium hydrohalides, or complexes of zirconium hydroxychloride and of aluminium hydroxychloride, with or without an amino acid, such as those described in U.S. Pat. No. 3,792,068.

Mention may in particular be made, among the aluminium salts, of aluminium chlorohydrate in the activated or nonactivated form, aluminium chlorohydrex, the aluminium chlorohydrex polyethylene glycol complex, the aluminium chlorohydrex propylene glycol complex, aluminium dichlorohydrate, the aluminium dichlorohydrex polyethylene glycol complex, the aluminium dichlorohydrex propylene glycol complex, aluminium sesquichlorohydrate, the aluminium sesquichlorohydrex polyethylene glycol complex, the aluminium sesquichlorohydrex propylene glycol complex or aluminium sulphate buffered with sodium aluminium lactate.

Mention may in particular be made, among aluminium zirconium salts, of aluminium zirconium octachloro-hydrate, aluminium zirconium pentachlorohydrate, aluminium zirconium tetrachlorohydrate or aluminium zirconium trichlorohydrate.

The complexes of zirconium hydroxychloride and of aluminium hydroxychloride with an amino acid are generally known under the name ZAG (when the amino acid is glycine). Mention may be made, among these products, of the aluminium zirconium octachlorohydrex glycine, aluminium zirconium pentachlorohydrex glycine, aluminium zirconium tetrathiorohydrex glycine and aluminium zirconium trichlorohydrex glycine complexes.

Use will more particularly be made of aluminium chlorohydrate in the activated or nonactivated form.

The antiperspirant salts or complexes can be present in the composition according to the invention in a proportion of approximately 0.5 to 25% by weight, with respect to the total weight of the composition.

Formulation Forms

The invention also relates to an aqueous scenting composition comprising, in a cosmetically acceptable medium:
a) at least 0.3% by weight, with respect to the total weight of the composition, of a scenting substance;
b) at least the said particles;
c) water.

The composition according to the invention can be provided in all the formulation forms conventionally used for a topical application and in particular in the form of aqueous gels or of aqueous or aqueous/alcoholic solutions. They can also, by addition of a fatty or oily phase, be provided in the form of dispersions of the lotion type, of emulsions with a liquid or semiliquid consistency of the milk type, obtained by dispersion of a fatty phase in an aqueous phase (O/W) or vice versa (W/O), or of suspensions or emulsions with a soft, semisolid or solid consistency of the cream or gel type, or also of multiple (W/O/W or O/W/O) emulsions, of microemulsions, of vesicular dispersions of ionic and/or nonionic type, or of wax/aqueous phase dispersions. These compositions are prepared according to the normal methods.

The invention applies not only to scenting products but also to products for the care or treatment of the skin, including the scalp, and lips, comprising an odorous substance. The composition according to the invention can thus constitute a composition for scenting, caring for or treating keratinous substances and can in particular be provided in the form of eau fraiche, eau de toilette, eau de parfum, aftershave lotion, care water, silicone or aqueous/silicone care oil or anhydrous cream. It can also be provided in the form of a scented two-phase lotion (eau de toilette phase/hydrocarbon oil and/or silicone oil phase).

The invention also relates to compositions packaged in a device equipped with an openwork wall, in particular a grating, packaged in a device equipped with a ball applicator (roll-on) or packaged in the form of sticks, characterized in that they comprise at least perlite particles as defined above. In this respect, they comprise the ingredients generally used in products of this type which are well known to a person skilled in the art.

According to another specific form of the invention, the scenting compositions according to the invention can be anhydrous.

Anhydrous composition is understood to mean a composition comprising less than 2% by weight of water, indeed even less than 0.5% by weight of water, and in particular devoid of water, the water not being added during the preparation of the composition but corresponding to the residual water contributed by the mixed ingredients.

According to a specific form of the invention, the scenting compositions according to the invention can also be provided in the form of an anhydrous cream.

According to a specific form of the invention, the scenting compositions according to the invention can also be provided in the form of a loose or compact powder.

According to a specific form of the invention, the scenting compositions according to the invention can also be provided in the form of an aerosol or of a spray in a pump-action spray.

Emulsifiers

The compositions according to the invention intended for cosmetic use can comprise at least one aqueous phase. They are in particular formulated as aqueous lotions, as a water-in-oil or oil-in-water emulsion or as a multiple emulsion (oil-inwater-in-oil or water-in-oil-in-water triple emulsion) (such emulsions are known and described, for example, by C. Fox in "Cosmetics and Toiletries", November 1986, Vol. 101, pages 101-112). They generally comprise one or more emulsifiers.

a) Oil-in-Water Emulsifiers

Mention may be made, as emulsifiers which can be used in oil-in-water emulsions or oil-in-water-in-oil triple emulsions, for example, of nonionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids; oxyalkylenated (oxyethylenated and/or oxypropylenated) ethers of fatty alcohols; sugar esters, such as sucrose stearate; and their mixtures, such as the mixture of glyceryl stearate and of PEG-40 stearate.

Mention may also be made of fatty alcohol/alkylpolyglycoside emulsifying mixtures, such as are described in Applications WO 92/06778, WO 95/13863 and WO 98/47610, for example the commercial products sold by SEPPIC under the MONTANOV® names.

b) Water-in-Oil Emulsifiers

Mention may be made, among the emulsifiers which can be used in water-in-oil emulsions or water-in-oil-in-water-in-oil triple emulsions or triple emulsions, by way of example, of alkyl dimethicone copolyols corresponding to the following formula (I):

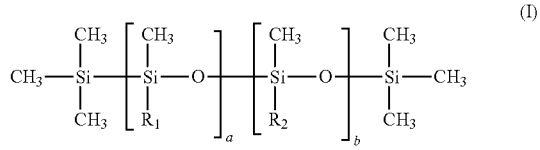

in which:
$R_1$ denotes a linear or branched $C_{12}$-$C_{20}$ and preferably $C_{12}$-$C_{18}$ alkyl group;
$R_2$ denotes the group: —$C_nH_{2n}$—(—$OC_2H_4$—)$_x$—(—$OC_3H_6$—)$_y$—O—$R_3$;
$R_3$ denotes a hydrogen atom or a linear or branched alkyl radical comprising from 1 to 12 carbon atoms;
a is an integer ranging from 1 to approximately 500;
b denotes an integer ranging from 1 to approximately 500;
n is an integer ranging from 2 to 12 and preferably from 2 to 5;
x denotes an integer ranging from 1 to approximately 50 and preferably from 1 to 30;
y denotes an integer ranging from 0 to approximately 49 and preferably from 0 to 29, with the proviso that, when y is other than zero, the ratio x/y is greater than 1 and preferably varies from 2 to 11.

Mention will more particularly be made, among the preferred alkyl dimethicone copolyol emulsifiers of formula (I), of Cetyl PEG/PPG-10/1 Dimethicone and more particularly the Cetyl PEG/PPG-10/1 Dimethicone and Dimethicone mixture (INCI name), such as the product sold under the trade name Abil EM90 by Goldschmidt, or else the Polyglyceryl-4 Stearate and Cetyl PEG/PPG-10 (and) Dimethicone (and) Hexyl Laurate mixture, such as the product sold under the trade name Abil WE09 by the same company.

Mention may also be made, among water-in-oil emulsifiers, of the dimethicone copolyols corresponding to the following formula (II):

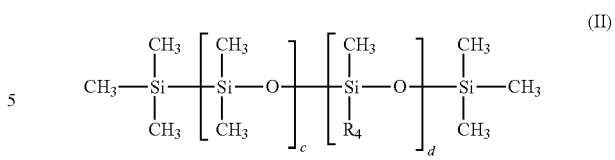

in which:
$R_4$ denotes the group: —$C_mH_{2m}$—(—$OC_2H_4$—)$_s$—(—$OC_3H_6$—)$_t$—O—$R_5$;
$R_5$ denotes a hydrogen atom or a linear or branched alkyl radical comprising from 1 to 12 carbon atoms;
c is an integer ranging from 1 to approximately 500;
d denotes an integer ranging from 1 to approximately 500;
m is an integer ranging from 2 to 12 and preferably from 2 to 5;
s denotes an integer ranging from 1 to approximately 50 and preferably from 1 to 30;
t denotes an integer ranging from 0 to approximately 50 and preferably from 0 to 30;
with the proviso that the sum s+t is greater than or equal to 1.

Use will particularly be made, among these preferred dimethicone copolyol emulsifiers of formula (II), of PEG-18/PPG-18 Dimethicone and more particularly the Cyclopentasiloxane (and) PEG-18/PPG-18 Dimethicone mixture (INCI name), such as the product sold by Dow Corning under the trade name Silicone DC 5225 C or KF-6040 from Shin-Etsu.

According to a particularly preferred form, use will be made of a mixture of at least one emulsifier of formula (I) and of at least one emulsifier of formula (II).

Use will more particularly be made of a mixture of PEG-18/PPG-18 Dimethicone and Cetyl PEG/PPG-10/1 Dimethicone and more particularly still of a mixture of Cyclopentasiloxane (and) PEG-18/PPG-18 Dimethicone and of Cetyl. PEG/PPG-10/1 Dimethicone and Dimethicone or of Polyglyceryl-4 Stearate and Cetyl. PEG/PPG-10 (and) Dimethicone (and) Hexyl Laurate.

Mention may also be made, among water-in-oil emulsifiers, of nonionic emulsifiers derived from fatty acid and from polyol, alkylpolyglycosides (APG), sugar esters and their mixtures.

Use may in particular be made, as nonionic emulsifiers derived from fatty acid and from polyol, of esters of fatty acid and of polyol, the fatty acid having in particular a $C_8$-$C_{24}$ alkyl chain and the polyols being, for example, glycerol and sorbitan.

Mention may in particular be made, as esters of fatty acid and of polyol, of esters of isostearic acid and of polyols, esters of stearic acid and of polyols, and their mixtures, in particular the esters of isostearic acid and of glycerol and/or of sorbitan.

Mention may in particular be made, as esters of stearic acid and of polyols, of the polyethylene glycol esters, such as PEG-30 Dipolyhydroxystearate, such as the product sold under the name Arlacel P135 by ICI.

Mention may be made, as esters of glycerol and/or of sorbitan, for example of polyglycerol isostearate, such as the product sold under the name Isolan GI 34 by Goldschmidt; sorbitan isostearate, such as the product sold under the name Arlacel 987 by ICI; sorbitan isostearate and glycerol, such as the product sold under the name Arlacel 986 by ICI; the mixture of sorbitan isostearate and of polyglycerol (3 mol) isostearate sold under the name Arlacel 1690 by Uniqema; and their mixtures.

The emulsifier can also be chosen from alkylpolyglycosides having an HLB of less than 7, for example those represented by the following general formula (1):

R—O-(G)$_x$         (1)

in which R represents a branched and/or unsaturated alkyl radical comprising from 14 to 24 carbon atoms, G represents a reduced sugar comprising from 5 to 6 carbon atoms and x denotes a value ranging from 1 to 10 and preferably from 1 to 4, and G denotes in particular a glucose, fructose or galactose.

The unsaturated alkyl radical can comprise one or more ethylenic unsaturations and in particular one or two ethylenic unsaturations.

Mention may be made, as alkylpolyglycosides of this type, of alkylpolyglucosides (G=glucose in the formula (1)) and in particular the compounds of formula (1) in which R more particularly represents an oleyl radical (unsaturated C18 radical) or an isostearyl radical (saturated C18 radical), G denotes glucose and x is a value ranging from 1 to 2, in particular isostearyl glucoside, oleyl glucoside and their mixtures. This alkylpolyglucoside can be used as a mixture with a coemulsifier, more especially with a fatty alcohol and in particular a fatty alcohol having the same fatty chain as that of the alkylpolyglucoside, that is to say comprising from 14 to 24 carbon atoms and having a branched and/or unsaturated chain, for example isostearyl alcohol when the alkylpolyglucoside is isostearyl glucoside and oleyl alcohol when the alkylpolyglucoside is oleyl glucoside, optionally in the form of a self-emulsifying composition, such as described, for example, in the document WO-A-92/06778. Use may be made, for example, of the isostearyl glucoside and isostearyl alcohol mixture sold under the name Montanov WO 18 by SEPPIC and the octyldodecanol and octyldodecyl xyloside mixture sold under the name Fludanov 20X by SEPPIC.

Mention may also be made of polyolefins comprising a succinic ending, such as polyisobutylenes comprising an esterified succinic ending and their salts, in particular the diethanolamine salts, such as the products sold under the names Lubrizol 2724, Lubrizol 2722 and Lubrizol 5603 by Lubrizol or the commercial product Chemcinnate 2000.

The total amount of emulsifiers in the composition will preferably be in the composition according to the invention at active material contents ranging from 1 to 8% by weight and more particularly from 2 to 6% by weight, with respect to the total weight of the composition.

Aqueous Phase

The aqueous phase of the aqueous scenting compositions of the invention comprises water and generally other solvents which are soluble or miscible in water. The solvents which are soluble or miscible in water comprise short-chain, for example $C_1$-$C_4$, monoalcohols, such as ethanol or isopropanol; or diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Use will more particularly be made of propylene glycol and glycerol, 1,3 propane diol.

Fatty Phase

The compositions according to the invention can comprise at least one water-immiscible liquid organic phase. The latter generally comprises one or more hydrophobic compounds which render the said phase immiscible in water. The said phase is liquid (in the absence of structuring agent) at ambient temperature (20-25° C.). Preferably, the water-immiscible liquid organic phase in accordance with the invention generally comprises at least one volatile oil and/or one nonvolatile oil and optionally at least one structuring agent.

"Oil" is understood to mean a fatty substance which is liquid at ambient temperature (25° C.) and atmospheric pressure (760 mmHg, i.e. 105 Pa). The oil can be volatile or nonvolatile.

"Volatile oil" is understood to mean, within the meaning of the invention, an oil capable of evaporating on contact with the skin or keratinous fibre in less than one hour, at ambient temperature and atmospheric pressure. The volatile oils of the invention are volatile cosmetic oils which are liquid at ambient temperature and which have a nonzero vapour pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

"Nonvolatile oil" is understood to mean an oil which remains on the skin or keratinous fibre, at ambient temperature and atmospheric pressure, for at least several hours and which has in particular a vapour pressure of less than $10^{-3}$ mmHg (0.13 Pa).

The oil can be chosen from any physiologically acceptable and in particular cosmetically acceptable oil, especially mineral, animal, vegetable or synthetic oils, in particular volatile or nonvolatile hydrocarbon and/or silicone and/or fluorinated oils and their mixtures.

More specifically, "hydrocarbon oil" is understood to mean an oil comprising mainly carbon and hydrogen atoms and optionally one or more functional groups chosen from hydroxyl, ester, ether or carboxyl functional groups. Generally, the oil exhibits a viscosity of 0.5 to 100 000 mPa·s, preferably of 50 to 50 000 mPa·s and more preferably of 100 to 300 000 mPa·s.

Mention may be made, as example of volatile oil which can be used in the invention, of those which were mentioned above in the section relating to volatile components.

Mention may be made, as example of nonvolatile oil which can be used in the invention, of:

hydrocarbon oils of animal origin, such as perhydrosqualene;

vegetable hydrocarbon oils, such as liquid triglycerides of fatty acids having from 4 to 24 carbon atoms, such as triglycerides of heptanoic or octanoic acids or also wheat germ, olive, sweet almond, palm, rapeseed, cottonseed, alfalfa, poppy, pumpkinseed, cucumber, blackcurrant seed, evening primrose, millet, barley, quinoa, rye, safflower, candlenut, passionflower, musk rose, sunflower, maize, soybean, grape seed, sesame, hazelnut, apricot, macadamia, castor or avocado oils, triglycerides of caprylic/capric acids, such as those sold by Stéarineries Dubois or those sold under the names Miglyol 810, 812 and 818 by Dynamit Nobel, jojoba oil or shea butter;

linear or branched hydrocarbons of mineral or synthetic origin, such as liquid paraffins and their derivatives, liquid petrolatum, polydecenes, polybutenes, hydrogenated polyisobutene, such as Parleam, or squalane;

synthetic ethers having from 10 to 40 carbon atoms;

synthetic esters, in particular of fatty acids, such as oils of formula $R_1COOR_2$ in which $R_1$ represents the residue of a linear or branched higher fatty acid comprising from 1 to 40 carbon atoms and $R_2$ represents a hydrocarbon chain, in particular a branched hydrocarbon chain, comprising from 1 to 40 carbon atoms with $R_1+R_2 \geq 10$, such as, for example, Purcellin oil (cetearyl octanoate), isononyl isononanoate, isopropyl myristate, isopropyl palmitate, $C_{12}$ to $C_{15}$ alkyl benzoate, hexyl laurate, diisopropyl adipate, isononyl isononanoate, 2-ethylhexyl palmitate, 2-octyldodecyl stearate, 2-octyldodecyl erucate, isostearyl isostearate or tridecyl trimellitate;

octanoates, decanoates or ricinoleates of alcohols or polyalcohols, such as propylene glycol dioctanoate; hydroxylated esters, such as isostearyl lactate, octyl hydroxystearate, octyldodecyl hydroxystearate, diisostearyl malate, triisocetyl citrate or heptanoates, octanoates, decanoates of fatty alcohols; polyol esters, such as propylene glycol dioctanoate, neopentyl glycol diheptanoate or diethylene glycol diisononanoate; and pentaerythritol esters, such as pentaerythrityl tetraisostearate;

fatty alcohols which are liquid at ambient temperature and which comprise a branched and/or unsaturated carbon chain having from 12 to 26 carbon atoms, such as octyldodecanol, isostearyl alcohol, 2-butyloctanol, 2-hexyldecanol, 2-undecylpentadecanol or oleyl alcohol;

higher fatty acids, such as oleic acid, linoleic acid or linolenic acid;

carbonates;

acetates;

citrates;

fluorinated oils which optionally comprise a hydrocarbon and/or silicone part, such as fluorosilicone oils, fluoropolyethers or fluorosilicones, such as described in the document EP-A-847752;

silicone oils, such as nonvolatile linear or cyclic polydimethylsiloxanes (PDMSs); polydimethylsiloxanes comprising pendant alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyl(trimethyl-siloxy)diphenylsiloxanes, diphenyl dimethicones, diphenyl(methyldiphenyl)trisiloxanes or (2-phenyl-ethyl)trimethylsiloxysilicates, and their mixtures.

Structuring Agent

The compositions according to the invention comprising a fatty phase can additionally comprise at least one structuring agent for the said fatty phase which can preferably be chosen from waxes, pasty compounds, inorganic or organic lipophilic gelling agents and their mixtures.

It is understood that the amount of these compounds can be adjusted by a person skilled in the art so as not to be detrimental to the effect desired in the context of the present invention.

Wax(es)

The wax is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

Within the meaning of the invention, the melting point corresponds to the temperature of the most endothermic peak observed by thermal analysis (DSC) as described in Standard ISO 11357-3; 1999. The melting point of the wax can be measured using a differential scanning calorimeter (DSC), for example the calorimeter sold under the name "MDSC 2920" by TA Instruments.

The Measurement Protocol is as Follows:

A 5 mg sample of wax placed in a crucible is subjected to a first rise in temperature ranging from −20° C. to 100° C. at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of wax is measured as a function of the temperature. The melting point of the compound is the value of the temperature corresponding to the tip of the peak of the curve representing the variation in the difference in power absorbed as a function of the temperature.

The waxes capable of being used in the compositions according to the invention are chosen from waxes of animal, vegetable, mineral or synthetic origin, and their mixtures, which are solid at ambient temperature.

Mention may in particular be made, by way of illustration of the waxes suitable for the invention, of hydrocarbon waxes, such as beeswax, lanolin wax and Chinese insect waxes; rice bran wax, carnauba wax, candelilla wax, ouricury wax, alfa wax, berry wax, shellac wax, Japan wax and sumac wax; montan wax, orange and lemon waxes, refined sunflower wax, sold under the name sunflower wax by Koster Keunen, microcrystalline waxes, paraffin waxes and ozokerite; polyethylene waxes, the waxes obtained by the Fischer-Tropsch synthesis and waxy copolymers, and their esters.

Mention may also be made of waxes obtained by catalytic hydrogenation of animal or vegetable oils having linear or branched $C_8$-$C_{32}$ fatty chains. Mention may in particular be made, among these, of isomerized jojoba oil, such as the transisomerized partially hydrogenated jojoba oil manufactured or sold by Desert Whale under the commercial reference Iso-Jojoba-50®, hydrogenated sunflower oil, hydrogenated castor oil, hydrogenated coconut oil, hydrogenated lanolin oil and di(1,1,1-trimethylolpropane) tetrastearate, sold under the name of Hest 2T-4S® by Heterene.

Mention may also be made of silicone waxes ($C_{30}$-$_{45}$ alkyl dimethicone) or fluorinated waxes.

Use may also be made of the waxes obtained by hydrogenation of castor oil esterified with cetyl alcohol which are sold under the names of Phytowax Castor 16L64® and 22L73® by Sophim. Such waxes are described in Application FR-A-2 792 190.

Use may be made, as wax, of a $C_{20}$-$C_{40}$ alkyl (hydroxystearyloxy)stearate (the alkyl group comprising from 20 to 40 carbon atoms), alone or as a mixture.

Such a wax is sold in particular under the names "Kester Wax K 82 P®", "Hydroxypolyester K 82 P®" and "Rester Wax K 80 P®" by Koster Keunen.

Mention may in particular be made, as microwaxes which can be used in the compositions according to the invention, of carnauba microwaxes, such as that sold under the name of MicroCare 350® by Micro Powders, synthetic wax microwaxes, such as that sold under the name of MicroEase 114S® by Micro Powders, the microwaxes composed of a mixture of carnauba wax and of polyethylene wax, such as those sold under the names of MicroCare 300® and 310® by Micro Powders, the microwaxes composed of a mixture of carnauba wax and of synthetic wax, such as that sold under the name MicroCare 325® by Micro Powders, polyethylene microwaxes, such as those sold under the names of Micropoly 200®, 220®, 220L® and 250S® by Micro Powders, the commercial products Perfomalen 400 Polyethylene and Performalene 500-L Polyethylene from New Phase Technologies, Performalene 655 Polyethylene or paraffin waxes, such as the wax having the INCA name Microcristalline Wax and Synthetic Wax and sold under the trade name Microlease by Sochibo; or polytetrafluoroethylene microwaxes, such as those sold under the names of Microslip 519® and 519 L® by Micro Powders.

The composition according to the invention will preferably comprise a content of wax(es) ranging from 3 to 20% by weight, with respect to the total weight of the composition, in particular from 5 to 15% by weight and more particularly from 6 to 15% by weight.

Pasty Compounds

"Pasty compound" is understood to mean, within the meaning of the present invention, a lipophilic fatty compound which exhibits a reversible solid/liquid change in state, which exhibits an anisotropic crystalline arrangement in the solid state and which comprises, at a temperature of 23° C., a liquid fraction and a solid fraction.

The pasty compound is preferably chosen from synthetic compounds and compounds of vegetable origin. A pasty compound can be obtained by synthesis from starting materials of vegetable origin.

The pasty compound can advantageously be chosen from:
lanolin and its derivatives,
polymeric or nonpolymeric silicone compounds,
polymeric or nonpolymeric fluorinated compounds,
vinyl polymers, in particular:
olefin homopolymers,
olefin copolymers,
hydrogenated diene homopolymers and copolymers,
linear or branched oligomers which are homo- or copolymers of alkyl(meth)acrylates preferably having a $C_8$-$C_{30}$ alkyl group,
oligomers which are homo- and copolymers of vinyl esters having $C_8$-$C_{30}$ alkyl groups,
oligomers which are homo- and copolymers of vinyl ethers having $C_8$-$C_{30}$ alkyl groups,
fat-soluble polyethers resulting from the polyetherification between one or more $C_2$-$C_{100}$, preferably $C_2$-$C_{50}$, diols,
esters,
their mixtures.

Preference is in particular given, among esters, to:
esters of an oligomeric glycerol, in particular diglycerol esters, in particular condensates of adipic acid and of glycerol, for which a portion of the hydroxyl groups of the glycerols have reacted with a mixture of fatty acids, such as stearic acid, capric acid, stearic acid, isostearic acid and 12-hydroxystearic acid, such as in particular those sold under the Softisan 649 brand by Sasol,
arachidyl propionate, sold under the Waxenol 801 brand by Alzo,
phytosterol esters,
triglycerides of fatty acids and their derivatives,
pentaerythritol esters,
noncrosslinked polyesters resulting from the polycondensation between a linear or branched $C_4$-$C_{50}$ dicarboxylic acid or polycarboxylic acid and a $C_2$-$C_{50}$ diol or polyol,
ester aliphatic esters resulting from the esterification of an aliphatic hydroxycarboxylic acid ester by an aliphatic carboxylic acid,
polyesters resulting from the esterification, by a polycarboxylic acid, of an aliphatic hydroxycarboxylic acid ester, the said ester comprising at least two hydroxyl groups, such as the products Risocast DA-H® and Risocast DA-L®,
dimer diol and dimer diacid esters, if appropriate esterified on their free alcohol or acid functional group(s) by acid or alcohol radicals, such as Plandool-G,
their mixtures.

The choice will preferably be made, among pasty compounds of vegetable origin, of a mixture of soybean sterols and of oxyethylenated (5 EO)/oxypropylenated (5 PO) pentaerythritol sold under the reference Lanolide by Vevy.

Lipophilic Gelling Agents

Inorganic Gelling Agents

Mention may be made, as inorganic lipophilic gelling agent, of optionally modified clays, such as hectorites modified by a $C_{10}$ to $C_{22}$ ammonium chloride, such as hectorite modified by distearyldimethylammonium chloride, such as, for example, that sold under the name Bentone 38V® by Elementis.

Mention may also be made of pyrogenic silica optionally hydrophobically treated at the surface, the size of the particles of which is less than 1 µm. This is because it is possible to chemically modify the surface of the silica by chemical reaction which results in a decrease in the number of silanol groups present at the surface of the silica. Silanol groups can in particular be replaced by hydrophobic groups: a hydrophobic silica is then obtained. The hydrophobic groups can be trimethylsiloxyl groups, which are obtained in particular by treatment of pyrogenic silica in the presence of hexamethyldisilazane. Silicas thus treated are named "Silica silylate" according to the CTFA (8th edition, 2000). They are, for example, sold under the references Aerosil R812® by Degussa or Cab-O-Sil TS-530® by Cabot, dimethylsilyloxyl or polydimethylsiloxane groups, which are obtained in particular by treatment of pyrogenic silica in the presence of polydimethylsiloxane or dimethyldichlorosilane. Silicas thus treated are named "Silica dimethyl silylate" according to the CTFA (8th edition, 2000). They are, for example, sold under the references Aerosil R972® and Aerosil R974® by Degussa and Cab-O-Sil TS-610® and Cab-O-Sil TS-720® by Cabot.

The hydrophobic pyrogenic silica exhibits in particular a particle size which can be from nanometric to micrometric, for example ranging approximately from 5 to 200 nm.

Organic Gelling Agents

The polymeric organic lipophilic gelling agents are, for example, partially or completely crosslinked organopolysiloxane elastomers with a three-dimensional structure, such as those sold under the names of KSG6®, KSG16® and KSG18® by Shin-Etsu, of Trefil E-505C® and Trefil E-506C® by Dow Corning, of Gransil SR-CYC®, SR DMF10®, SR-DC556®, SR 5CYC Gel®, SR DMF 10 Gel® and SR DC 556 Gel® by Grant Industries and of SF 1204® and JK 113® by General Electric; ethylcellulose, such as that sold under the name Ethocel® by Dow Chemical; galactomannans comprising from one to six and in particular from two to four hydroxyl groups per monosaccharide and substituted by a saturated or unsaturated alkyl chain, such as guar gum alkylated by $C_1$ to $C_6$ and in particular $C_1$ to $C_3$ alkyl chains, and their mixtures; or block copolymers of "diblock", "triblock" or "radial" type of the polystyrene/poly-isoprene or polystyrene/polybutadiene type, such as those sold under the name Luvitol HSB® by BASF, of the polystyrene/copoly (ethylene-propylene) type, such as those sold under the name Kraton® by Shell Chemical Co., or of the polystyrene/copoly (ethylene-butylene) type, or blends of triblock and radial (star) copolymers in isododecane, such as those sold by Penreco under the name Versagel®, such as, for example, the blend of butylene/ethylene/styrene triblock copolymer and of ethylene/propylene/styrene star copolymer in isododecane (Versagel M 5960).

Mention may also be made, as lipophilic gelling agent, of polymers with a weight-average molecular weight of less than 100 000 comprising a) a polymer backbone having hydrocarbon repeat units provided with at least one heteroatom and optionally b) at least one optionally functionalized pendant fatty chain and/or at least one optionally functionalized terminal fatty chain having from 6 to 120 carbon atoms and being bonded to these hydrocarbon units, such as described in Applications WO-A-02/056847, WO-A-02/47619, the contents of which are incorporated by way of reference, in particular polyamide resins (especially comprising alkyl groups having from 12 to 22 carbon atoms), such as those described in U.S. Pat. No. 5,783,657, the content of which is incorporated by way of reference.

Mention may also be made, among the lipophilic gelling agents which can be used in the compositions according to the invention, of esters of dextrin and of fatty acid, such as dextrin palmitates, in particular such as those sold under the names Rheopearl TL® and Rheopearl KL® by Chiba Flour.

Use may also be made of silicone polyamides of the polyorganosiloxane type, such as those described in the documents U.S. Pat. No. 5,874,069, U.S. Pat. No. 5,919,441, U.S. Pat. No. 6,051,216 and U.S. Pat. No. 5,981,680.

These silicone polymers can belong to the following two families:

polyorganosiloxanes comprising at least two groups capable of establishing hydrogen bond interactions, these two groups being situated in the chain of the polymer, and/or polyorganosiloxanes comprising at least two groups capable of establishing hydrogen bond interactions, these two groups being situated on grafts or branchings.

Suspending Agents

In order to improve the homogeneity of the product, use may additionally be made of one or more suspending agents which are preferably chosen from hydrophobic modified montmorillonite clays, such as hydrophobic modified bentonites or hectorites. Mention may be made, for example, of the product Stearaikonium Bentonite (CTFA name) (reaction product of bentonite and of the quaternary ammonium stearalkonium chloride), such as the commercial product sold under the name Tixogel MP 250 by Sud Chemie Rheologicais, United Catalysts, Inc., or the product Disteardimonium Hectorite (CTFA name) (reaction product of hectorite and of distearyldimonium chloride), sold under the name of Bentone 38 or Bentone Gel by Elementis Specialities.

The suspending agents are preferably present in amounts ranging from 0.1 to 5% by weight and more preferably from 0.2 to 2% by weight, with respect to the total weight of the composition.

Organic Powder

According to a specific form of the invention, the antiperspirant compositions according to the invention will additionally comprise an organic powder.

In the present patent application, "organic powder" is understood to mean any solid which is insoluble in the medium at ambient temperature (25° C.)

Mention may be made, as organic powders which can be used in the composition of the invention, for example, of polyamide particles and in particular those sold under the Orgasol names by Atochem; polyethylene powders; microspheres based on acrylic copolymers, such as those made of ethylene glycol dimethacrylate/lauryl methacrylate copolymer sold by Dow Corning under the name of Polytrap; polymethyl methacrylate microspheres, sold under the name Microsphere M-100 by Matsumoto or under the name Covabead LH85 by Wackherr; hollow polymethyl methacrylate microspheres (particle size: 6.5-10.5 μm) sold under the name Ganzpearl GMP 0800 by Ganz Chemical; methyl methacrylate/ethylene glycol dimethacrylate copolymer microbeads (size: 6.5-10.5 μm) sold under the name Ganzpearl GMP 0820 by Ganz Chemical or Microsponge 5640 by Amcol Health & Beauty Solutions; ethylene/acrylate copolymer powders, such as those sold under the name Flobeads by Sumitomo Seika Chemicals; expanded powders, such as hollow microspheres, in particular the microspheres formed of a terpolymer of vinylidene chloride, of acrylonitrile and of methacrylate sold under the name Expancel by Kemanord Plast under the references 551 DE 12 (particle size of approximately 12 μm and density of 40 kg/m$^3$), 551 DE 20 (particle size of approximately 30 μm and density of 65 kg/m$^3$) and 551 DE 50 (particle size of approximately 40 μm) or the microspheres sold under the name Micropearl F 80 ED by Matsumoto; powders formed of natural organic materials, such as powders formed of starch, in particular of crosslinked or noncrosslinked maize, wheat or rice starches, such as the powders formed of starch crosslinked with octenylsuccinic anhydride sold under the name Dry-Flo by National Starch; silicone resin microbeads, such as those sold under the name Tospearl by Toshiba Silicone, in particular Tospearl 240; amino acid powders, such as the lauroyllysine powder sold under the name Amihope LL-11 by Ajinomoto; wax microdispersion particles which preferably have mean dimensions of less than 1 μm and in particular ranging from 0.02 μm to 1 μm and which are essentially composed of a wax or of a mixture of waxes, such as the products sold under the name Aquacer by Byk Cera, in particular Aquacer 520 (mixture of synthetic and natural waxes), Aquacer 514 or 513 (polyethylene wax) or Aquacer 511 (polymer wax), or such as the products sold under the name Jonwax 120 by Johnson Polymer (mixture of polyethylene and paraffin waxes) and under the name Ceraflour 961 by Byk Gera (micronized modified polyethylene wax); and their mixtures.

Other Additives

The composition of the invention can additionally comprise any additive normally used in the field of scenting and/or deodorant compositions chosen in particular from cosmetic or dermatological active principles, emollients or softeners, moisturizing agents, such as glycerol, soothing agents, such as α-bisabolol, allantoin or aloes vera, vitamins, propellants, fillers, pearlescent agents, glitter, dyes soluble in the vehicle of the composition, stabilizers of the colour of the fragrance and their mixtures. When they are present in the composition of the invention, these additives can be present in an amount ranging from 0.001 to 10% by weight and better still from 0.01 to 5% by weight, with respect to the total weight of the composition.

The composition of the invention can additionally comprise dyes soluble in the vehicle of the said composition.

Mention may be made, as soluble dyes in accordance With the invention, of water-soluble or hydrophilic dyes, such as: caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, cochineal carmine (CI 15850, CI-75470), Ext. Violet 2, Red 6-7, Ferric Ferrocyanide, Ultramarines, Acid Yellow 3/Yellow 10, Acid Blue 3 or Yellow 10.

The soluble dye or dyes in accordance with the invention are preferably present in amounts ranging from $10^{-5}$ to 1% of the total weight of the composition, preferably from $10^{-4}$ to 0.1% of the total weight of the composition.

Mention will be made, as stabilizers of the colour of fragrances, of Tris(tetramethylhydroxypiperidinol) citrate, such as the product sold under the name "Tinogard Q" by Ciba-Geigy, Sodium Benzotriazolyl Butylphenol Sulfonate, such as the product sold under the name "Tinogard HS" by Ciba-Geigy, Benzotriazole Dodecyl p-Cresol, such as the product sold under the name "Tinogard TL" by Ciba-Geigy, such as the product sold under the trade name "Cibafast H Liquid" by Ciba-Geigy, or Bumetrizole, such as the product sold under the name "Tinogard AS" by Ciba-Geigy.

According to a specific form of the invention, use will additionally be made of at least one antioxidant and/or at least one peptizing agent, so as to improve the clearness of the composition and/or to reduce, indeed even eliminate, phenomena of precipitation under cold conditions which can be caused by some fragrances and/or improve the stability of the composition on storage.

Mention may be made, among antioxidants, for example, of BHA (tert-butyl-4-hydroxyanisole), BHT (2,6-di(tert-butyl)-p-cresol) or tocopherols, such as vitamin E and its derivatives, such as tocopheryl acetate. They are used at concentrations ranging from 0.01% to 1%, with respect to the total weight of the composition.

Use will more particularly be made, among the peptizing agents which can be used according to the invention, of the hydrogenated castor oil oxyethylenated with 60 mol of ethylene oxide: INCI name: PEG-60 Hydrogenated Castor Oil, such as the product sold under the trade name Cremaphor RH60 by BASF. They are used at concentrations ranging from 0.1% to twice the concentration of fragrance concentrate, with respect to the total weight of the composition.

Of course, a person skilled in the art will take care to choose the optional additional additives and/or their amounts in such a way that the advantageous properties of the composition according to the invention are not, or not substantially, detrimentally affected by the envisaged addition.

Aerosols

The compositions according to the invention can also be pressurized and be packaged in an aerosol device composed of:
(A) a container comprising an antiperspirant composition as defined above,
(B) at least one propellant and one means for dispensing the said aerosol composition.

The propellants generally used in products of this type, which are well known to a person skilled in the art, are such as, for example, dimethyl ether (DME), volatile hydrocarbons, such as n-butane, propane or isobutane, and their mixtures, optionally with at least one chlorinated and/or fluorinated hydrocarbon; mention may be made, among the latter, of the compounds sold by Dupont de Nemours under the Freon® and Dymel® names, in particular monofluorotrichloromethane, difluorodi-chloromethane, tetrafluorodichloroethane and 1,1-di-fluoroethane, sold in particular under the trade name Dymel 152 A by Dupont. Use may also be made, as propellant, of carbon dioxide gas, nitrous oxide, nitrogen or compressed air.

The compositions comprising the perlite particles as defined above and the propellant or propellants can occur in the same compartment or in different compartments in the aerosol container. According to the invention, the concentration of propellant generally varies from 5 to 95% by weight under pressure and more preferably from 50 to 85% by weight, with respect to the total weight of the pressurized composition.

The dispensing means, which forms a part of the aerosol device, is generally composed of a dispensing valve controlled by a dispensing head, itself comprising a nozzle via which the aerosol composition is vaporized. The container comprising the pressurized composition can be opaque or transparent. It can be made of glass, of polymer or of metal, optionally covered with a protective lacquer layer.

The invention will now be described with reference to the following examples, given by way of illustration and without implied limitation. In these examples, unless otherwise indicated, the amounts are expressed as percentages by weight. The following scenting formulations were prepared; the amounts are shown as percentages by weight.

EXAMPLES

Comparative Test on Tenacity of the Fragrance

The tenacity of the fragrance at 8 hours and 24 hours of the following deodorant aerosols was evaluated:

| Ingredients | 1 (invention) | 2 (outside the invention) |
| --- | --- | --- |
| Fragrance (Masc E_0621398/01, sold by Mane) | 1.0 | 1.0 |
| Expanded milled perlite (Optimat 1430 OR, World Minerals) | 1.0 | — |
| Ethanol | q.s. for 100 | q.s. for 100 |
| Isobutane | 55 | 55 |

Formulations 1 and 2 are sprayed for 2 seconds into paper cups. These cups are stored at ambient temperature for 8 hours.

Twenty subjects then evaluate the intensity of the fragrance detected and answer the following question: "The intensity of the odour is, in your opinion: Nonexistent—Very faint—Faint—Moderate—Fairly strong—Strong—Very strong".

The same question is again posed after 24 hours.

A fragrance is considered to be tenacious if at least 60% of the answers are taken from the following descriptors: "Moderate—Fairly strong—Strong—Very strong".

Results at 8 Hours

| Example | Non-existent | Very faint | Faint | Moderate | Fairly strong | Strong | Very strong | Combined criteria |
| --- | --- | --- | --- | --- | --- | --- | --- | --- |
| 1 invention | 5% | 20% | 10% | 20% | 15% | 25% | 5% | 65% |
| 2 outside the invention | 0% | 25% | 25% | 5.0% | 30% | 15% | 0% | 50% |

Results at 24 Hours

| Example | Non-existent | Very faint | Faint | Moderate | Fairly strong | Strong | Very strong | Combined criteria |
|---|---|---|---|---|---|---|---|---|
| 1 invention | 5% | 30% | 35% | 20% | 5% | 5% | 0% | 60% |
| 2 outside the invention | 20% | 40% | 30% | 10% | 10% | 0% | 0% | 40% |

Example 3

Scented Anhydrous Deodorant Stick

| Ingredients (INCI name) | Amounts |
|---|---|
| Polyethylene Wax (Performalene 500-L Polyethylene, New Phase Technologies) | 4.1 |
| Ethylene Homopolymer (Performalene 400 Polyethylene, New Phase Technologies) | 8.3 |
| Isopropyl Palmitate | 28.5 |
| Isohexadecane | 19.6 |
| Dicaprylyl Carbonate (Cetiol CC, Cognis) | 6.0 |
| Undecane/Tridecane miwture according to example 1 or 2 of WO2008/155059 | 10.0 |
| Cyclopentadimethylsiloxane (Dow Corning 245 Fluid, Dow Corning) | 0 |
| Methyl Methacrylate Crosspolymer (Ganzpearl GMP 0820, Ganz Chemical) | 15.0 |
| Expanded Milled Perlite (Optimat 1430 OR, World Minerals) | 6.5 |
| Micronized Zinc Pyrrolidonecarboxylate (UCIB, Solabia) | 0.5 |
| Fragrance | 1.5 |

Example 4

Scented Antiperspirant Roll-On

| Ingredients (INCI name) | Amounts |
|---|---|
| Aluminium Chlorohydrate (Chlorhydrol 50, Summit Reheis) | 30 |
| Expanded Milled Perlite (Optimat 1430 OR, World Minerals) | 1 |
| Steareth-100/PEG-136/HDI Copolymer (Rheolate FX 1100, Elementis) | 1 |
| Polydimethylsiloxane (Viscosity: 350 cSt) (Dow Corning 200 Fluid 350 cSt, Dow Corning) | 0.5 |
| $C_{14-22}$ Alcohols (and) $C_{12-20}$ Alkyl Glucoside (Montanov L, SEPPIC) | 2.5 |
| Fragrance | 1.0 |
| Preservative | q.s. |
| Deionized water | q.s. for 100 |

Example 5

Scented Deodorant Aerosol

| Ingredients (INCI name) | Amounts |
|---|---|
| Triethyl Citrate (Citroflex 2, Reilly Chemicals) | 1.0 |
| Stearalkonium Bentonite (Tixogel MP 250, Süd Chemie Rheolog.) | 0.2 |
| Isopropyl Palmitate | 0.9 |
| Expanded Milled Perlite (Optimat 1430 OR, World Minerals) | 2.6 |
| Cyclopentadiniethylsiloxane (Dow Corning 245 Fluid, Dow Corning) | 9.0 |
| Cyclopentasiloxane (and) Dimethiconol (Dow Corning 1501 Fluid, Dow Corning) | 1.3 |
| Fragrance | 1.0 |
| Isobutane (A-31, Aeropres) | q.s. for 100 |

Example 6

Scented Anhydrous Deodorant Cream

| Ingredients (INCI name) | Amounts as % by weight |
|---|---|
| Triethyl Citrate (Citroflex 2, Reilly Chemicals) | 7.0 |
| Isopropyl Palmitate | 6.0 |
| Expanded Milled Perlite (Optimat 1430 OR, World Minerals) | 17.5 |
| Cyclopentasiloxane (and) Dimethiconol (Dow Corning 1501 Fluid, Dow Corning) | 9.0 |
| Fragrance | 1.0 |
| Cyclopentadimethylsiloxane (Dow Corning 245 Fluid, Dow Corning) | q.s. for 100 |

The Optimat ® 1430 OR is dispersed in the mixture of the other starting materials using a paddle. A homogeneous paste is obtained.

The invention claimed is:
1. A method for treating human axillary odor associated with perspiration comprising:
applying to skin of a human in need thereof, a deodorant and/or antiperspirant composition; and
treating the human axillary odor associated with perspiration by masking the axillary odor and/or reducing perspiration;
wherein the deodorant and/or antiperspirant composition is in the form of a solid stick or is applied to the human using a pressurized aerosol device or a roll-on applicator; and wherein the deodorant and/or antiperspirant composition comprises at least 0.3% by weight of at least one fragrance scenting substance, and comprises expanded amorphous perlite particles having a particle size defined by a median diameter D50 ranging from 0.5 to 50 µm.

2. A method according to claim 1, wherein the expanded amorphous perlite particles comprise at least two elements chosen from silicon, aluminium, and magnesium.

3. A method according to claim 1, wherein the expanded amorphous perlite particles are obtained by thermal expansion of a volcanic rock comprising from 1 to 10% by weight of water and less than 10% by weight of crystalline rock, with respect to the total weight of the composition of the rock, followed by a milling.

4. A method according to claim 1, wherein the amount of expanded amorphous perlite particles used represents from 1 to 60% by weight of the total weight of the composition.

5. A method according to claim 1, wherein the composition comprises at least one deodorant active principle in addition to the at least one fragrance and/or at least one antiperspirant active principle in addition to expanded amorphous perlite particles.

6. A method according to claim 1, wherein the composition comprises water.

7. The method according to claim 2, where the expanded amorphous perlite particles are obtained by thermal expansion of a volcanic rock comprising from 1 to 10% by weight of water and less than 10% by weight of crystalline rock, with respect to the total weight of the composition of the rock, followed by a milling.

8. The method according to claim 1 where the amount of expanded amorphous perlite particles used represents from 5 to 60% by weight of the total weight of the composition.

9. The method according to claim 1, wherein the composition is free from dyes.

10. The method according to claim 1, wherein the method comprises applying an antiperspirant composition, wherein the antiperspirant composition comprises, in addition to the expanded amorphous perlite particles, at least one additional antiperspirant active principle.

11. The method according to claim 1, wherein the method comprises applying a deodorant composition, wherein the deodorant composition comprises, in addition to the fragrance, at least one additional deodorant active principle.

12. The method according to claim 1, wherein the deodorant and/or antiperspirant composition is anhydrous and in the form of a solid stick.

13. The method according to claim 1, wherein the deodorant and/or antiperspirant composition is applied to the human using a pressurized aerosol device.

14. The method according to claim 1, wherein the deodorant and/or antiperspirant composition is applied to the human using a roll-on applicator.

* * * * *